United States Patent [19]

Nagabhushan et al.

[11] Patent Number: 4,921,941

[45] Date of Patent: May 1, 1990

[54] ORALLY ACTIVE ANTIANDROGENS

[75] Inventors: Tattanahalli L. Nagabhushan, Parsippany; Martin F. Haslanger, Ridgewood; Michael F. Czarniecki, Westfield, all of N.J.

[73] Assignee: Schering Corporation, Kenilworth, N.J.

[21] Appl. No.: 68,509

[22] Filed: Jul. 1, 1987

[51] Int. Cl.$^5$ .............................................. C07K 5/08
[52] U.S. Cl. ..................................... 530/331; 530/330; 530/828
[58] Field of Search ..................... 530/330, 331, 828; 514/18, 19, 625, 2

[56] References Cited

U.S. PATENT DOCUMENTS

| | | | |
|---|---|---|---|
| 3,875,229 | 4/1975 | Gold | 564/202 |
| 3,995,060 | 11/1976 | Neri et al. | 514/625 |
| 4,139,638 | 2/1979 | Neri et al. | 514/626 |
| 4,154,727 | 5/1979 | Hirai et al. | 530/332 |
| 4,161,540 | 7/1979 | Neri et al. | 514/626 |
| 4,239,776 | 12/1980 | Glen et al. | 514/522 |
| 4,329,364 | 5/1982 | Neri et al. | 514/626 |
| 4,386,080 | 5/1983 | Crossley et al. | 514/522 |
| 4,535,092 | 8/1986 | Hughes | 514/438 |
| 4,636,505 | 1/1987 | Tucker | 514/256 |

FOREIGN PATENT DOCUMENTS

| | | | |
|---|---|---|---|
| 0056565 | 7/1982 | European Pat. Off. | 514/18 |
| 0108709 | 8/1981 | Japan | 514/18 |
| 811145 | 4/1981 | PCT Int'l Appl. | |

OTHER PUBLICATIONS

Peptide Hormones, 1976, pp. 1–7.
Organic Chemistry, Morrison & Boyd, 3rd ed., pp. 1149–1160.
Katchen et al, J. Clin. Endocrin. and Metab., 41 (1975), pp. 373–379.
*The Concise Chemical and Technical Dictionary*, H. Bennet, ed. (Chemical Publishing Co., Inc., 1974) p. XXIV.
*Invest Urol.*, 10 (1972), pp. 123–130.
*Endocrinology*, 91 (1972), pp. 427–437.
*Abstracts of the 1984 ICAAC*, Abstract 315.

*Primary Examiner*—Lester L. Lee
*Assistant Examiner*—T. D. Wessendorf
*Attorney, Agent, or Firm*—Anita W. Magatti; Henry C. Jeanette

[57] ABSTRACT

Antiandrogenic peptidyl esters, particularly tri-peptidyl esters, of the active metabolite of flutamide are disclosed.

16 Claims, No Drawings

ORALLY ACTIVE ANTIANDROGENS

SUMMARY OF THE INVENTION

The present invention relates to novel peptidyl esters of 2-hydroxy-N-phenylalkanamide derivatives useful as antiandrogenic agents for the treatment of prostatic carcinoma, benign prostatic hypertrophy, hirsutism, acne and related disorders.

The invention also relates to a method of treating androgen-dependent disease conditions comprising administering to a mammal in need of such treatment an antiandrogenic effective amount of a peptidyl ester of a 2-hydroxy-N-phenylalkanamide derivative.

Another aspect of the invention relates to pharmaceutical compositions comprising an antiandrogenic effective amount of a peptidyl ester of a 2-hydroxy-N-phenylalkanamide derivative and a pharmaceutically acceptable carrier.

In particular, the invention relates to tripeptidyl esters of 2-hydroxy-N-phenylalkanamide derivatives, wherein the preferred derivative is 2-hydroxy-2-methyl-N-[4-nitro-3-(trifluoromethyl)phenyl]propanamide.

BACKGROUND OF THE INVENTION

Flutamide, 2-methyl-N-[4-nitro-3-(trifluoromethyl)phenyl]propanamide (previously known as 4'-nitro-3'-trifluoromethylisobutyranilide), and related substituted N-phenylamides are known antiandrogens, effective in the treatment of prostatic carcinoma, benign prostatic hypertrophy, acne and hirsutism. See U.S. Pat. Nos. 4,329,364; 3,995,060; 4,139,638; and 4,161,540, all to Neri et al.

Also known as antiandrogens are hydroxy- and alkanoyloxy-substituted N-phenylamides such as 2-hydroxy-2-methyl-N-[(4-substituted and 3,4-disubstituted)phenyl]propanamides. See Gold, U.S. Pat. No. 3,875,229, herein incorporated by reference, wherein 2-hydroxy-2-methyl-N-[4-nitro-3-(trifluoromethyl)phenyl]-propanamide is indicated to be a preferred species. Said compound has been identified as the major active metabolite of flutamide. See Katchen et al, *J. Clin. Endocrin. and Metab.*, 41 (1975), p. 373-9.

Other related antiandrogens include N-phenylalkanamides containing a cyano substituent on the phenyl ring (see U.S. Pat. No. 4,239,776 to Glen et al), (N-phenyl)phenylalkanamides (see U.S. Pat. No. 4,386,080 to Cressley et al), (N-phenyl)heterocyclylalkanamides (see U.S. Pat. No. 4,535,092 to Hughes), and (N-phenyl)phenylsulfonylalkanamides (see U.S. Pat. No. 4,636,505 to Tucker).

DETAILED DESCRIPTION

The compounds of this invention are represented by the formula

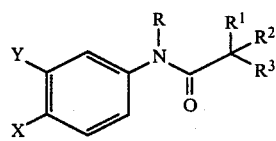

wherein
X is CN, $NO_2$, $CF_3$, Cl, Br or I;
Y is F, Cl, Br, I, F, $NO_2$, $NH_2$, $CF_3$ or CN;
R is H or lower alkyl;
$R_1$ and $R_2$ are independently straight or branched alkyl radicals having up to eight carbon atoms, $R_1$ and $R_2$ together with the carbon to which they are attached form a cyclopropyl or cyclobutyl ring, or one of $R_1$ and $R_2$ is alkyl as defined above and the other is aryl, arylalkyl or aryl-$S(O)_{0-2}$alkyl, wherein the aryl group is unsubstituted or is substituted by 1-3 substituents selected from the group consisting of H, halogen, $NO_2$, $CO_2H$, $CONH_2$, CN, lower alkyl, alkoxy, alkanoyl, lower akylsulfenyl, lower alkylsulfinyl, lower alkylsulfonyl, perfluoro lower alkylsulfinyl, perfluoro lower alkylsulfonyl, alkoxycarbonyl, phenyl, phenylsulfenyl, phenylsulfinyl or phenylsulfonyl;

$R_3$ is a di-, tri- or tetra-peptidyl group comprising 2–4 amino acids independently selected from naturally occuring amino acids, which peptidyl group is joined to the molecule by a C-terminal amino acid residue; and the pharmaceutically acceptable salts thereof.

As used herein, the term "lower alkyl" refers to straight or branched chain alkyl groups having 1 to 4 carbon atoms. Similarly, the term "alkoxy" and "alkanoyl" refer to groups having chain lengths of 1-4 carbon atoms. The term "perfluoro lower alkyl" refers to alkyl groups in which at least one of the carbon atoms is totally fluorinated, e.g. trifluoromethyl, $\alpha,\alpha$-difluoroethyl and $\beta,\beta,\beta$-trifluoroethyl. "Aryl" refers to phenyl or naphthyl rings.

The di-, tri- or tetra-peptidyl groups are comprised of naturally occurring amino acids joined to each other by conventional peptide (i.e., —CONH—) bonds and joined to the rest of the molecule through a C-terminal amino acid residue, i.e. a —COO— group. Examples of naturally occurring amino acids are proline, sarcosine (N-methylglycine), alanine, arginine, asparagine, aspartic acid, cysteine, glutamine, glutamic acid, glycine, histidine, isoleucine, leucine, lysine, methionine, phenylalanine, serine, threonine, tryptophan, tyrosine and valine.

Preferred compounds of formula I are those wherein Y is trifluoromethyl and X is nitro, iodo, bromo, chloro or cyano, with nitro and cyano being more preferred. Another group of preferred compounds are those wherein X is nitro and Y is bromo or chloro. A third group of preferred compounds are those wherein R is hydrogen. Still another group of preferred compounds are those wherein $R^1$ and $R^2$ are each methyl. A further group of preferred compounds are those wherein $R^1$ is methyl and $R^2$ is aryl-$S(O)_{0-2}$alkyl, especially wherein $R^2$ is 4-fluorophenylsulfonylmethyl. Especially preferred are compounds of formula I wherein R is hydrogen, X is nitro, Y is trifluoromethyl, and $R^1$ and $R^2$ are each methyl. Also, especially preferred are compounds wherein R is hydrogen, X is cyano, Y is trifluoromethyl, $R^1$ is methyl and $R^2$ is 4-fluorophenylsulfonylmethyl.

Tri-peptidyl esters are preferred. Preferred amino acids are lysine, glycine, proline, alanine and sarcosine. Preferred tri-peptide groups are alanine-glycine-sarcosine, lysine-glycine-sarcosine, and lysine-glycine-proline, with the latter being more preferred.

Preferred compounds of the invention are L-lysyl-glycyl-N-methylglycine, [1-methyl-[[4-nitro-3-(trifluoromethyl)phenyl]aminocarbonyl]ethyl]ester;

L-alanyl-glycyl-N-methylglycine, [1-methyl-[[4-nitro-3-(trifluoromethyl)phenyl]aminocarbonyl]ethyl]-ester; and L-lysyl-glycyl-L-proline, [1-methyl-[[4-nitro-3-(trifluoromethyl)phenyl]aminocarbonyl]ethyl]ester. Also preferred are the corresponding peptidyl esters of 2-hydroxy-2-methyl-3-(4-fluorophenylsulphonyl)-N-[4-cyano-3-(trifluoromethyl)phenyl]propanamide.

Compounds of this invention may form acid addition salts with pharmaceutically acceptable acids such as hydrochloric, hydrobromic, methane sulfonic, toluenesulfonic and sulfuric acids.

Compounds of this invention may possess one or more asymmetric carbon atoms, e.g. in compounds wherein $R^1$ and $R^2$ are different, and in compounds wherein one or more of the amino acids comprising $R^3$ contain a chiral center. All stereoisomers are contemplated as a part of this invention. Preferred for $R^3$ are amino acids in the L-configuration.

Compounds of the invention are prepared by methods well known in the art. A preferred method comprises reacting a 2-hydroxy-N-phenylalkanamide derivative of formula II

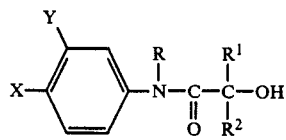

II wherein X, Y, R, $R^1$ and $R^2$ are as defined above, with the carboxy group of an N-protected amino acid, then adding on one or more amino acids by conventional peptide condensation reactions to obtain the peptidyl ester. Alternatively, the carboxy group of a di-, tri- or tetrapeptidyl group may be directly reacted with a compound of formula II. The reaction of a compound of formula II with the carboxy group of an N-protected amino acid is carried out at 0°–25° C. in an inert solvent such as dichloromethane in the presence of a base such as 4-N,N-dimethylaminopyridine and a condensing agent such as 1-(3-dimethylaminopropyl)-3-ethylcarbodiimide (DEC). The subsequent addition of an amino acid or a peptide is similarly carried out at 0°–25° C. in an inert solvent such as dimethylformamide in the presence of a base such as triethylamine and condensing agents such as DEC and 1-hydroxybenzotriazole (HOBT).

The known coupling methods include amino group protection during the coupling reaction, for example with a protecting group such as N-t-butoxycarbonyl (BOC), followed by removal of the protecting group to yield compounds of formula I.

Starting materials of formula II are known (See U.S. Pat. No. 3,875,229 and U.S. Pat. No. 4,636,505 cited above). Amino acids and di-, tri- and tetra-peptides are known or may be prepared by well known methods.

Following is an example of a preparation of a tri-peptidyl ester of formula I. Those skilled in the art will recognize that by modifying this procedure, e.g. by using different amino acids or by increasing or decreasing the number of amino acids, other compounds of formula I may be prepared.

EXAMPLE

L-lysyl-glycyl-L-proline-[1-methyl-[[4-nitro-3-(trifluoromethyl)phenyl]aminocarbonyl]ethyl]ester, dihydrochloride A. Bis-$N_\alpha,N_\epsilon$-t-BOC-L-lysine succinimidyl ester Dissolve bis-$N_\alpha,N_\epsilon$-t-BOC-L-lysine (6.2 g), N-hydroxysuccinimide (2.8 g) and N,N-dicyclohexylcarbodiimide (5.1 g) in 1,2 dimethoxyethane (20 ml) and stir at 0° C. for 12 hr. Filter the reaction mixture and evaporate the filtrate to dryness. Stir residual oil at 0° with ether and filter to obtain the title compound as a crystalline product (8.2 g).

B. (Bis-$N_\alpha,N_\epsilon$-t-BOC-L-Lysyl)glycine

Dissolve the product of Step A (4.4 g) in dimethylformamide (DMF)(32 ml) and add to a solution of glycine (0.75 g) and sodium bicarbonate (1.7 g) in water (24 ml). Stir at 0° C. for 2 hours and then at room temperature for 12 hours. Remove the solvent in vacuo and dissolve the residue in water. Adjust the pH to 3.5 using aqueous hydrochloric acid and extract the resultant solution with ethyl acetate. Wash the ethyl acetate with water and saturated brine solution and dry with sodium sulfate. Evaporate the ethyl acetate to obtain the title compound (3.5 g). Calculated for $C_{18}H_{33}N_3O_7$: C=53.53%; H=8.17%; N=10.41%. Found: C=53.16%; H=8.43%; N=10.70%.

C. (N-t-BOC-L-Proline)-[1-methyl-[[4-nitro-3-(trifluoromethyl)phenyl]aminocarbonyl]ethyl]ester Dissolve 1-methyl-[(4-nitro-3-trifluoromethyl)phenyl]aminocarbonyl]ethanol (3.5 g), N-t-BOC-L-proline (2.6 g), 4-dimethylaminopyridine (0.70 g) and DEC (2.1 g) in dichloromethane (120 ml). Stir at 0° C. for 2 hours, then for 5 days at room temperature. Evaporate the solvent, dissolve the resultant residue in ethyl acetate and wash the ethyl acetate successively with saturated sodium bicarbonate, water, and saturated brine solution. Dry the ethyl acetate with sodium sulfate and evaporate to a syrup. Chromatograph the product on silica gel, eluting with dichloromethane:ethyl acetate (99:1) to obtain the title compound (4.2 g). Calculated for $C_{21}H_{26}N_3O_7F_3$: C=51.53%; H=5.35%; N=8.58%. Found: C=51.63%; H=5.28%; N=8.31%.

D.

L-Proline-[1-methyl-[[4-nitro-3-trifluoromethyl)phenyl]aminocarbonyl]ethyl]ester, hydrochloride Dissolve the product of Step C (3.6 g) in dioxane (10 ml), cool to 0° and add 35 ml of saturated HCl in dioxane. Stir at 0° for 1 hour and then at room temperature for 1 hour. Evaporate the solvent, add ethyl ether and stir at 0° for 12 hours. Filter the solid to obtain the title compound (2.8 g). Calculated for $C_{16}H_{19}N_3O_5ClF_3$: C=45.13%; H=4.49%; N=9.87%. Found: C=45.56%; H=4.80%; N=9.41%.

E.

(Bis-$N_\alpha,N_\epsilon$-t-BOC-L-lysyl)-glycyl-proline[1-methyl-[(4-nitro-3-trifluoromethyl)phenyl]aminocarbonyl]ethyl]ester Dissolve the product of Step B (1.6 g) and the product of Step D (1.5 g) in DMF (35 ml), add HOBT (0.65 g), DEC (1.2 g) and triethylamine (1.3 ml). Stir at 0° for 12 hours. Evaporate the solvent in vacuo and dissolve the resultant residue in ethyl acetate. Wash the ethyl acetate successively with 10% aqueous citric acid, water, saturated sodium bicarbonate solution, water and saturated brine solution. Dry the ethyl acetate with sodium sulfate and evaporate the solvent to obtain the title compound (2.4 g). Calculated for $C_{34}H_{49}N_6O_{11}F_3$: C=52.70%; H=6.37%; N=10.84%. Found: C=52.66%; H=6.43%; N=10.43%.

F. Dissolve the product of Step E (2.1 g) in dioxane (5 ml) at 0° C. and add saturated HCl in dioxane (45 ml). Stir for 1 hour at 0° C., add additional saturated HCl in dioxane (20 ml) and stir for 1 hour at room temperature. Evaporate the dioxane in vacuo and triturate the resultant residue with ether. Filter the solid to obtain the title compound (1.6 g). Calculated for $C_{24}H_{35}N_6O_7Cl_2F_3$: C=44.51%; H=5.44%; N=12.98%. Found: C=44.90%; H=5.75%; N=12.49%.

The antiandrogenic activity of flutamide and its active metabolite are well documented. However, we have surprisingly found that the peptidyl esters of this invention demonstrate superior bioavailability compared to flutamide, its active metabolite, or to simple esters of the active metabolite, e.g. 2-hydroxy-2-methyl-N-[4-nitro-3-(trifluoromethyl)phenyl]propanamide acetate (hereinafter acetyl flutamide).

The following Table 1 shows that all amino acid esters tested, especially the tri-peptidyl esters, delivered the active metabolite of flutamide more efficiently than either the active metabolite itself or simple esters of the active metabolite:

TABLE 1

Plasma Concentrations (ng/ml)[a] of Flutamide Active Metabolite in Rats After Administration of Various Esters Thereof Compound $O_2N-\underset{F_3C}{\underset{|}{\bigcirc}}-\underset{|}{\overset{H}{N}}-\overset{O}{\underset{\|}{C}}-\underset{R}{\overset{}{\bigg\langle}}$

| R | Concentration | | | Relative Rank |
|---|---|---|---|---|
| | 2 Hours | 4 Hours | 0–4 Hours | |
| H (flutamide) | 715 | 974 | 2404 | 1.00 |
| OH (metabolite) | 183[b] | 810 | 1176 | 0.49 |
| OAc | 142 | 278 | 562 | 0.23 |
| ala—gly—sar | 1952 | 1115 | 5019 | 2.09 |
| lys—gly—sar | 1103 | 1248 | 3454 | 1.44 |
| pro | 1059 | 1393 | 3511 | 1.46 |
| sar | 1345 | 958 | 3648 | 1.52 |
| lys—gly—pro | 2277 | 1847 | 6401 | 2.66 |

[a] All concentrations are average of 2 animals and normalized to a 5 mg/kg dose of flutamide active metabolite.
[b] Value from one animal Plasma concentrations of the flutamide active metabolite were determined by gas-liquid chromatography in 300–350 gram male Sprague Dawley rats following single oral 5 mg/kg doses of the compounds listed. Areas under the 0–4 hour plasma level curves were calculated for each compound and compared to the area obtained for flutamide active metabolite as shown in the last column of the table above.

Using a similar method, the plasma concentrations of flutamide active metabolite after administration of the two most active peptidyl esters from Table 1 and flutamide itself were determined over a period of sixteen hours, as shown in Table 2.

TABLE 2

Plasma Concentrations (ng/ml)[a] of Flutamide Active Metabolite for up to 16 Hours

| Ester | 0.5 hr | 1 hr | 2 hr | 4 hr | 8 hr | 16 hr | 0—16 hr | Relative Rank |
|---|---|---|---|---|---|---|---|---|
| - (flutamide) | 210 | 322 | 614 | 722 | 649 | 236 | 8272 | 1.00 |
| ala—gly—sar | 1079 | 2029 | 1365 | 1803 | 1005 | 423 | 17240 | 2.08 |
| lys—gly—pro | 1392 | 1907 | 1751 | 1170 | 1054 | 256 | 15611 | 1.89 |

[a] All concentrations are average of 3 animals and normalized to a 5 mg/kg dose of flutamide active metabolite.

For the treatment, i.e., the reduction or elimination of androgenic conditions, in particular prostatic carcinoma, compounds of this invention should be administered at a rate which provides a quantity of flutamide active metabolite equivalent to a dose of about 1 to 30 mg per kg of body weight per day, preferably about 2 to about 20 mg per kg of body weight per day. The aforementioned doses may be divided into two or more portions for administration over the course of the day, for example, one-third of the daily dose administered three times a day. Pharmaceutical preparations for a 70 kilogram mammal should provide a daily dose of flutamide active metabolite of about 100 mg to about 2000 mg, preferably about 250 mg to about 1500 mg, and more preferably about 500 mg to about 1000 mg, and should be continued until symptomatic relief is obtained, as ascertained by the attending diagnostician.

The pharmaceutical preparations of this invention include such oral dosage forms as tablets, capsules and elixirs as well as parenteral dosage forms, e.g. ampuls and vials.

Additionally, they may be in the form of suppositories (both rectal and urethral). In tablet form, a compound of this invention is compounded with an inert pharmaceutical carrier which may contain a suitable binder, such as gums, starches, and sugars. The ingredients may also be incorporated into gelatin capsules or formulated into elixirs which have the advantage of being susceptible to manipulations in flavor by the addition of standard natural or synthetic flavoring agents. Highly satisfactory administration may also be achieved in the form of aqueous parenteral suspension.

Preferably, the aforementioned formulations are so proportioned as to afford a unit dose of about 125 or about 250 mg of flutamide active metabolite. Thus, for example, a preferred dosage of 750 mg per day could thus be administered as one 250 mg tablet or capsule three times per day or two 125 mg tablets or capsules three times per day.

Representative formulations for compounds of this invention are as follows, wherein "Drug" refers to a peptide ester of flutamide active metabolite:

| TABLET FORMULATION | |
|---|---|
| Ingredients | Milligrams per Tablet |
| Drug | 250.00 |
| Lactose, anhydrous | 221.70 |
| Sodium lauryl sulfate | 15.00 |
| Microcrystalline cellulose | 100.00 |
| Starch | 162.50 |
| Water (evaporates) | (0.29) |
| Silica Gel (Syloid 244) | 0.40 |
| Magnesium stearate | 0.40 |
| Tablet Weight | 750.00 |

| PARENTERAL SUSPENSION FORMULATION | |
|---|---|
| Ingredients | Milligrams per Milliliter |
| Drug | 250.00 |
| Methyl Cellulose 15 cps. U.S.P. | 0.25 |
| Sodium Citrate, Dihydrate | 30.00 |
| Benzyl Alcohol, NF | 9.00 |
| Methylparaben, U.S.P. | 1.80 |
| Propylparaben, U.S.P. | 1.20 |
| Water for Injection, U.S.P. q.s.a.d. | 1.00 |

| CAPSULE FORMULATION | | | |
|---|---|---|---|
| Ingredients | Milligrams/Capsule | | |
| Drug | 125 | 250 | 200 |
| Lactose, hydrous, USP | 360.5 | 235.5 | 185 |
| Sodium Lauryl Sulfate, NF | 12 | 12 | 12 |
| Povidone, USP (Polyvinylpyrrolidone) | 25 | 25 | 25 |
| Water, Purified, USP (evap.) or S.D. Alcohol, 3-A (evap.)* | | | |
| Corn Starch (Food Grade) | 77 | 77 | 77 |
| Magnesium Stearate, NF | 0.5 | 0.5 | 1.0 |
| Full Weight (mg.) | 600 | 600 | 500 |

*Approximately 75 ml. 3-A alcohol/100 capsules, or 60 ml. water/1000 capsules

We claim:
1. A compound represented by the formula

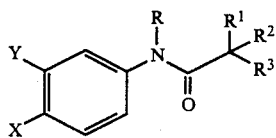

wherein
X is CN, NO$_2$, CF$_3$, Cl, Br or I;
Y is F, Cl, Br, I, NO$_2$, NH$_2$, CF$_3$ or CN;
R is H or lower alkyl;
R$_1$ and R$_2$ are independently straight or branched alkyl radicals having up to eight carbon atoms, R$_1$ and R$_2$ together with the carbon to which they are attached form a cyclopropyl or cyclobutyl ring, or one of R$_1$ and R$_2$ is alkyl as defined above and the other is aryl, arylalkyl or aryl-S(O)$_{0-2}$alkyl, wherein the aryl group is unsubstituted or is substituted by 1–3 substituents selected from the group consisting of H, halogen, NO$_2$, CO$_2$H, CONH$_2$, CN, lower alkyl, alkoxy, alkanoyl, lower alkylsulfenyl, lower alkylsulfinyl, lower alkylsulfonyl, perfluoro lower alkylsulfinyl, perfluoro lower alkylsulfonyl, alkoxycarbonyl, phenyl, phenylsulfenyl, phenylsulfinyl and phenylsulfonyl;
R$_3$ is a tri-peptidyl group selected from the group consisting of alanyl-glycyl-sarcosyl, lysyl-glycyl-sarcosyl and lysyl-glycyl-prolyl, which peptidyl group is joined to the molecule by a C-terminal amino acid residue; and the pharmaceutically acceptable salts thereof.
2. A compound of claim 1 wherein R is hydrogen.
3. A compound of claim 1 wherein X is nitro, iodo, bromo, chloro or cyano.
4. A compound of claim 3 wherein X is nitro or cyano.
5. A compound of claim 1 wherein Y is trifluoromethyl.
6. A compound of claim 4 wherein Y is trifluoromethyl.
7. A compound of claim 6 wherein R is hydrogen.
8. A compound of claim 1 wherein R$^1$ and R$^2$ are each methyl.
9. A compound of claim 7 wherein R$^1$ and R$^2$ are each methyl.
10. A compound of claim 1 wherein R$^1$ is methyl and R$^2$ is 4-fluorophenylsulfonylmethyl.
11. A compound of claim 7 wherein R$^1$ is methyl and R$^2$ is 4-fluorophenylsulfonylmethyl.
12. A compound of claim 1 wherein R$_3$ is lysyl-glycyl-prolyl.
13. A compound of claim 7 selected from the group consisting of: L-lysyl-glycyl-N-methylglycine, [1-methyl-[[4-nitro-3-(trifluoromethyl)phenyl]aminocarbonyl]ethyl]ester; L-alanyl-glycyl-N-methylglycine, [1-methyl-[[4-nitro-3-(trifluoromethyl)phenyl]aminocarbonyl]ethyl]ester; L-lysyl-glycyl-L-proline, [1-methyl-[[4-nitro-3-(trifluoromethyl)phenyl]aminocarbonyl]ethyl]ester; L-lysyl-glycyl-N-methylglycine, [1-(4-fluorophenylsulfonylmethyl)-1-methyl-[[4-cyano-3-trifluoromethyl)phenyl]aminocarbonyl]ethyl]ester; alanyl-glycyl-N-methylglycine, [1-(4-fluorophenylsulfonylmethyl)-1-methyl-[[4-cyano-3-trifluoromethyl)phenyl]aminocarbonyl]ethyl]ester; and L-lysyl-glycyl-L-proline, [1-(4-fluorophenylsulfonylmethyl)-1-methyl-[[4-cyano-3-trifluoromethyl)phenyl]aminocarbonyl]ethyl]ester.
14. An antiandrogenic pharmaceutical composition comprising an antiandrogen-effective amount of a compound of claim 1 in a pharmaceutically acceptable carrier.
15. A composition of claim 14 for oral administration.
16. A composition of claim 15 wherein the compound is selected from the group consisting of L-lysyl-glycyl-N-methylglycine, [1-methyl-[[4-nitro-3-(trifluoromethyl)phenyl]aminocarbonyl]ethyl]ester; L-alanyl-glycyl-N-methylglycine, [1-methyl-[[4-nitro-3-(trifluoromethyl)phenyl]aminocarbonyl]ethyl]ester; L-lysyl-glycyl-L-proline, [1-methyl-[[4-nitro-3-(trifluoromethyl)phenyl]aminocarbonyl]ethyl]ester; L-lysyl-glycyl-N-methylglycine, [1-(4-fluorophenylsulfonylmethyl)-1-methyl-[[4-cyano-3-trifluoromethyl)phenyl]aminocarbonyl]ethyl]ester; alanyl-glycyl-N-methylglycine, [1-(4-fluorophenylsulfonylmethyl)-1-methyl-[[4-cyano-3-trifluoromethyl)phenyl]aminocarbonyl]ethyl]ester; and L-lysyl-glycyl-L-proline [1-(4-fluorophenylsulfonylmethyl)-1-methyl-[[4-cyano-3-trifluoromethyl)phenyl]aminocarbonyl]ethyl]ester.

* * * * *